(12) United States Patent
Ebnet et al.

(10) Patent No.: US 10,806,902 B2
(45) Date of Patent: Oct. 20, 2020

(54) PUNCTURING SYSTEM

(71) Applicants: Jens Ebnet, Hamburg (DE); Roland Moelgen, Hannover (DE); Konstantinos Raymondos, Hannover (DE)

(72) Inventors: Jens Ebnet, Hamburg (DE); Roland Moelgen, Hannover (DE); Konstantinos Raymondos, Hannover (DE)

( * ) Notice: Subject to any disclaimer, the term of this patent is extended or adjusted under 35 U.S.C. 154(b) by 93 days.

(21) Appl. No.: 15/748,240

(22) PCT Filed: Jul. 26, 2016

(86) PCT No.: PCT/EP2016/067785
§ 371 (c)(1),
(2) Date: Jan. 29, 2018

(87) PCT Pub. No.: WO2017/017095
PCT Pub. Date: Feb. 2, 2017

(65) Prior Publication Data
US 2018/0214674 A1 Aug. 2, 2018

(30) Foreign Application Priority Data

Jul. 29, 2015 (DE) .......................... 10 2015 112 388
Oct. 21, 2015 (DE) .......................... 10 2015 117 923

(51) Int. Cl.
*A61M 25/06* (2006.01)
*A61M 25/00* (2006.01)
(Continued)

(52) U.S. Cl.
CPC ..... *A61M 25/0606* (2013.01); *A61B 17/3417* (2013.01); *A61B 90/40* (2016.02);
(Continued)

(58) Field of Classification Search
CPC .......... A61M 25/0606; A61M 25/0026; A61M 2025/0175; A61M 25/0111; A61M 2025/0004; A61B 90/40; A61B 17/3417
See application file for complete search history.

(56) References Cited

U.S. PATENT DOCUMENTS 5,176,653 A * 1/1993 Metals ................... A61B 17/34
604/167.02
5,752,969 A * 5/1998 Cunci .................... A61B 17/02
604/272

(Continued)

FOREIGN PATENT DOCUMENTS

DE 102 15 191 A1 10/2003
DE 10 2008 045 692 A1 3/2010
(Continued)

*Primary Examiner* — Lauren P Farrar
(74) *Attorney, Agent, or Firm* — W&C IP (57) ABSTRACT

The invention relates to a puncturing system comprising an outer tubular body which is designed to remain in a body part of a living being, characterized in that the puncturing system has at least one inner tubular body and a puncturing needle, wherein the inner tubular body is guided through a working lumen of the outer tubular body and can be longitudinally displaced with respect to the outer tubular body, and the puncturing needle is guided through a puncture lumen of the inner tubular body and the inner tubular body can be longitudinally displaced with respect to the puncturing needle, wherein, after a body part has been punctured by means of a puncturing section of the puncturing needle, which protrudes out of a patient-side end of the puncturing system, the inner tubular body can be moved out of the patient-side end of the catheter at least partially out of the outer tubular body, and is thereby designed to accommodate the puncturing section of the puncturing needle, which protrudes out of the patient-side end of the catheter, at least partially in the puncture lumen of the inner tubular body.

11 Claims, 3 Drawing Sheets

(51) Int. Cl.
*A61B 90/40* (2016.01)
*A61B 17/34* (2006.01)
*A61M 25/01* (2006.01)

(52) U.S. Cl.
CPC ..... *A61M 25/0026* (2013.01); *A61M 25/0111* (2013.01); *A61M 2025/0004* (2013.01); *A61M 2025/0175* (2013.01)

(56) References Cited

U.S. PATENT DOCUMENTS

| | | |
|---|---|---|
| 2004/0147877 A1 | 7/2004 | Heuser |
| 2009/0198218 A1 | 8/2009 | Gill et al. |
| 2013/0131610 A1* | 5/2013 | Dewaele .............. A61B 5/0215 604/264 |

FOREIGN PATENT DOCUMENTS

| | | |
|---|---|---|
| WO | 99/37354 A1 | 7/1999 |
| WO | 2011/089014 A1 | 1/2011 |
| WO | 2012/162677 A1 | 11/2012 |
| WO | 2013/138519 A1 | 9/2013 |

* cited by examiner

PUNCTURING SYSTEM

FIELD OF THE INVENTION

The invention relates to a puncture system having an outer tubular body configured to remain in a body part of a living being, such as e.g. a central venous catheter having a catheter tube which is configured to remain in a vein.

In view of jurisdictions in which treatment methods can be protected by patents, the invention further relates to improved methods for applying a puncture system such as e.g. a central venous catheter, in particular using the puncture system according to the invention such as e.g. the central venous catheter.

BACKGROUND

The central venous catheter is also referred to as central line or central venous line or central venous access catheter, or abbreviated CVC.

Performing a central venous catheterization is one of the most common medical measures overall. A CVC is a catheter which is introduced over a relatively large puncturable, so-called "peripheral vein" that is not immediately in the vicinity of the heart and the tip of said CVC comes to rest near the heart in a "central vein". Using said CVC, it is possible to infuse liquids and blood products, and also inject medicaments. Moreover, it is possible to obtain blood samples and measure the vein pressure. A central venous catheter can remain in the patient for weeks if there are no complications.

Applying a central venous catheter represents a routine method in in-hospital emergency medicine, anesthesiology and intensive care medicine. However, said catheter also finds use in other clinical fields, for example in oncology for applying chemotherapy agents and in intensive care medicine for high-calorie parenteral feeding, for example after gastrointestinal operations.

A central venous catheter allows the application of circulatory-system-stabilizing medicaments and other substances close to the heart, where they are immediately effective. Strongly concentrated infusion solutions such as electrolyte solutions and feeding solutions can often only be administered by way of a central venous catheter since they irritate smaller veins (e.g. veins in the back of the hand or arms) too strongly and hence would lead to inflammations and thromboses of the latter.

As a rule, a central venous catheter has, distant from the patient, one to five so-called "legs" (lumen), which merge into a common catheter tube toward the patient, said catheter tube being introduced into the vein. It consists of body-friendly material such as e.g. polyurethane which, moreover, imparts thermoplastic properties thereon. Thus, the catheter tube becomes softer upon heating to the body temperature. The insertion depth of the catheter tube from the level of the skin is approximately 15-20 cm in the case of adult patients, depending on the selected access path and on patient-specific factors such as height and weight.

A CVC is usually introduced into the body by means of the Seldinger technique, described in 1953, using a Seldinger wire. This technique has several disadvantages. On account of requiring a plurality of sequential work steps and a sterile work field, the patient and user risk injury and infection. The Seldinger wire may damage the heart and may cause arrhythmia; moreover, it may accidentally remain in the patient. Its orientation in the body may be unclear. Not least, the Seldinger technique is complicated to carry out and expensive. An application of this method outside of a hospital and in very restricted spatial conditions is therefore virtually impossible. Previously existing direct puncture techniques without a Seldinger wire have not prevailed in broad clinical application on account of only a catheter tube with a restricted diameter being insertable.

SUMMARY

The invention is therefore based on the object of specifying a puncture system, such as e.g. a central venous catheter, which can be applied more easily and more quickly to the patient.

In view of jurisdictions in which treatment methods can be protected by patents, the object is further based on the object of specifying improved methods for applying a puncture system such as e.g. a central venous catheter.

The aforementioned object is achieved by a central venous catheter having a catheter tube configured to remain in a vein, wherein the catheter has at least a cannula and a puncture needle, wherein the cannula is guided through a work lumen of the catheter tube and longitudinally displaceable in relation to the catheter tube, and the puncture needle is guided through a puncture lumen of the cannula and the cannula is longitudinally displaceable in relation to the puncture needle, wherein, after puncturing a vein by means of a puncturing portion of the puncture needle protruding from a patient-near end of the catheter, the cannula is able to be pushed, at least in part, out of the catheter tube from the patient-near end of the catheter, and, in the process, said cannula is embodied to receive the puncturing portion of the puncture needle protruding from the patient-near end of the catheter, at least in part, in the puncture lumen of the cannula.

The invention is advantageous in that the central venous catheter can be applied substantially more easily and quickly to the patient than known solutions. Here, it is possible to completely dispense With the Seldinger wire and the relatively time-consuming steps connected therewith. Here, the invention resorts to the basic principles of the Seldinger technique, which, by all means, are advantageous, but develops said technique such that the risks to the patient are minimized. As a result of the catheter having a multi-shell construction with a puncture needle arranged at the inside, a catheter tube arranged therearound on the outside and an intermediate layer in the form of the cannula and the individual layers of puncture needle/cannula/catheter tube or the work volume thereof being longitudinally displaceable in relation to one another, in principle in an arbitrary manner, an entirely new technique of applying a central venous catheter is facilitated. Here, after an appropriate puncture of a vein by means of the puncturing portion of the puncture needle, the cannula can be inserted into the vein through the opening formed thus. Here, the cannula already provides a protection for the vein against injury by the tip of the puncture needle. Moreover, the cannula thereafter acts as an insertion aid for the catheter tube into the vein since, in this state, it has a similar function to what the Seldinger wire had previously. However, in contrast to the Seldinger wire, the cannula can always be monitored in terms of its orientation and it can also be removed at any desired time. Likewise, the puncture needle can be withdrawn or entirely removed at any desired time.

A further advantage of the invention is that a single access by way of the central venous catheter according to the invention is now possible and sufficient in cases in which, previously, a plurality of peripheral venous vein accesses were created. On account of the complexity connected with the application of central venous catheters according to the prior art, use was previously made of a plurality of peripheral venous vein accesses instead of a central venous catheter in certain circumstances. Such disadvantageous situations may now also be improved by the invention described here. As a result of this, it is possible to reduce the risk of infection. The previously complex care of a plurality of vein accesses is simplified since only the one central venous access is still required. The overview when applying medicaments and hence the patient safety are also increased.

The central venous catheter according to the invention may be provided in different sizes, for example for humans with different sizes (adults/children).

Further, it was identified that the puncture system described above on the basis of the example of a central venous catheter may also otherwise be used in an advantageous manner for punctures on body parts. The described parts of the puncture system or of the central venous catheter remain as described above in this case, but they should be adapted, in particular in respect of length and optionally diameter, depending on the application.

Accordingly, the object specified at the outset is also achieved by a general puncture system according to claim 1. In comparison with the above-described application as a central venous catheter (or general catheter), the puncture system has an outer tubular body, which may be rigid or flexible, e.g. in the form of a duct or a tube, instead of a catheter tube. Further, the puncture system has an inner tubular body instead of a cannula. Said inner tubular body may also be embodied as a cannula, but this is not mandatory. Using such a puncture system, it is possible in comparison with the central venous catheter not only to puncture a vein but, in principle, any body part of a living being.

Accordingly, any hollow body as a body part of a living being to be punctured, for example bladder, windpipe or any type of vessel, in particular veins or arteries, may be advantageously punctured by the puncture system. Further, non-hollow bodies may advantageously also be punctured, e.g. organs or collections of liquids such as abscesses. Advantageously, organ interstitia may be punctured as well.

In this way, the following fields of application can be covered by the puncture system: angiology, cardiology, puncture of the pleural interstitium (liquids, air), urology, (interventional) radiology, tracheotomy and cricothyrotomy, implantation of cardiac support systems.

Here, it is advantageous if the puncture system or at least the outer tubular body is transparent. This allows an improved accessibility of the status of the puncture procedure, inter alia by way of the color and flow speed of the liquids flowing in the puncture system.

With this in mind, the following description, which orients itself on the example of a central venous catheter (or only a catheter), should also be understood in the sense that the applications and functions described therein, as well as the technical features, can also be realized by the puncture system within the general meaning thereof. In this light, the following description also relates to the puncture system in general; consequently, in general, catheter tube below also means the outer tubular body, cannula means the inner tubular body and vein means the above-explained body part of a living being to be punctured.

The puncture system according to the invention may also be used in combination with a Seldinger wire. Here, it is advantageous if a hollow Seldinger wire is used in this case, said Seldinger wire, in respect of length, being able to be embodied like a conventional Seldinger wire or in a shorter version. As a result of the design as a hollow Seldinger wire, it is possible to allow an aspiration of blood, liquid or air; consequently, the orientation of the hollow Seldinger wire can be verified in the region of the target structure before the puncture channel is widened. Moreover, a medicament may also already be injected via the introduced Seldinger wire in emergencies before the introduction of further elements of the puncture system, allowing important time to be saved. In the proximal direction, i.e. toward the user, the hollow Seldinger wire may be compatible with an aspiration aid, for example a syringe, optionally by way of an adapter that is already situated on the syringe. This is advantageous in that, initially, a spontaneous return flow via the hollow Seldinger wire may be awaited (pulsating, e.g. in the case of an incorrect arterial puncture) before the aspiration aid can be plugged on. Before the hollow Seldinger wire is introduced, the puncture needle should initially be withdrawn by way of the wire.

The puncture system according to the invention and, in particular, the outer tubular body thereof are configured to remain in a body part of a living being. Here, "remaining" means remaining in the conventional medical sense, as is applicable, for example, to a CVC, i.e. remaining within the scope of days or weeks or months. Here, the puncture system and, in particular, the outer tubular body thereof need not be held in position by a user, but, instead, they are also configured to remain within the meaning of being unable to cause damage when remaining to the human body. To this end, the outer tubular body is embodied, for example, from a thermoplastic, blunt, non-shearable material. Accordingly, the outer tubular body may be embodied as a tube or tubule. After applying the outer tubular body to a body part of a living being by means of the puncture system, the inner tubular body and the puncture needle are removed in their entirety from the outer tubular body such that, during the phase of remaining in the body part, only the outer tubular body remains there. On account of the expediently selected diameter ratios between outer tubular body, inner tubular body and puncture needle, the application of the puncture system in a body part of a living being is very easily possible, in particular without a skin incision.

For the purposes of fixing the puncture system and, in particular, the outer tubular body thereof to the body part of a living being, for example to the skin, adhesive bonding by means of a plaster or suturing to the skin may e.g. be effectuated. In an advantageous development of the invention, the puncture system has a click-clip mechanism for fixation on the skin. By way of such a click-clip mechanism, which may have a similar embodiment to clamps for a wound closure, fixation clamps can be bored into the skin by manual actuation, e.g. finger pressure from above, such that the puncture system is securely affixed to the skin. Time-consuming suturing of the puncture system may then be dispensed with.

In view of jurisdictions in which treatment methods can be protected by patents, the object set forth at the outset is moreover achieved by a method for applying a central venous catheter to a patient, in particular a catheter of the aforementioned type, including the following steps:

a) puncturing the vein of the patient by means of a puncturing portion of the puncture needle protruding from a patient-near end of the catheter, b) advancing the cannula in the vein, i.e. over the puncturing portion of the puncture needle, once the puncture needle has been correctly placed in the vein, c) advancing the catheter tube over the cannula placed in the vein such that the catheter tube is also inserted into the vein.

The puncture needle can be withdrawn or removed before or after the catheter tube is inserted into the vein. In particular, removing the puncture needle before the introduction of the catheter tube into the vein is advantageous in order to further minimize possible risks of injury. Finally, the cannula may also be removed by virtue of the latter being pulled out of the catheter tube at the patient-distant end. The puncture needle may be removed in the same way.

Here, initially only the essential steps were mentioned. Further steps that are expedient and required in practice, such as aspirating venous blood for monitoring the orientation of the puncture needle, affixing the components of the catheter and the like should also be carried out. An exemplary process of applying the central venous catheter will still be specified with further details below within the scope of the explanations of the exemplary embodiments.

According to an advantageous development of the invention, a longitudinal displacement of the catheter tube in relation to the cannula and a longitudinal displacement of the cannula in relation to the puncture needle is controllable independently of one another in each case by means of actuation means of a patient-distant end of the catheter. This further promotes the aforementioned, innovative technique of applying the catheter. By way of example, a syringe that is connected to the puncture needle at the patient-distant end may serve as actuation means for the longitudinal displacement of the puncture needle. By way of example, a fixing flag which is connected at the patient-distant end of the catheter to the cannula may serve as actuation means of the cannula.

According to an advantageous development of the invention, the catheter does not have a dilatation cannula. This is advantageous in that the catheter may be constructed in a simple manner and with few components, and said catheter, accordingly, is also simple to operate. In particular, there is no need for a separate operation of a dilatation cannula.

According to an advantageous development of the invention, the catheter, for the purposes of introducing the catheter tube into the vein at the patient-near end, has a dilatation body that increases in a ramp-shaped manner, through which the cannula is guided. This is advantageous in that the dilatation required for introducing the catheter tube into the vein can be performed in a simple manner by virtue of the dilatation body initially being pushed over the cannula into the body opening formed in this way. To this end, the dilatation body advantageously has a longitudinally displaceable embodiment in relation to the cannula. As a result of applying force when advancing the catheter tube, the dilatation body can, in the process, be advanced in relation to the cannula thereby. According to an advantageous development of the invention, the dilatation body is fastened to the catheter tube or part of the catheter tube. As a result of such a secure connection between the dilatation body and the catheter tube, the orientation of the dilatation body may also be monitored at all times. Thus, the dilatation body may be configured, for example, as a region of the catheter tube that has a ramp-shaped embodiment at the patient-near end of the catheter tube.

The part of the dilatation body that increases in a ramp-shaped manner may have an embodiment that increases in a linear or non-linear ramp-shaped manner. Further, it is advantageous if the dilatation body is made from a material with a low coefficient of friction, i.e. a particularly slidable material, or if it is at least coated with such a material. This may also minimize friction during the advance through the skin and consequently during the dilatation process.

As mentioned previously, the inner tubular body may be pushed, at least in part, out of the outer tubular body from the patient-near end of the puncture system after a body part has been punctured by means of a puncturing portion of the puncture needle protruding from the patient-near end of the puncture system. Consequently, the inner tubular body may be advanced to the patient in the process and may, in the process, readily be advanced into the body part of the living being as well and may penetrate the skin in the process. The outer tubular body may also be pushed distally toward the patient over the inner tubular body and may, in the process, also be readily advanced into the body part of the living being and may penetrate the skin in the process, in particular once the puncture needle has been removed or withdrawn.

According to an advantageous development of the invention, the catheter tube, at least outside of the vein, is surrounded by a first cover, said first cover keeping the catheter tube sterile outside of the vein. When the catheter tube is inserted into the vein, the first cover is pushed back as a consequence of the skin contact at the patient, and so the catheter tube reaches the vein in a sterile state. This is not connected to any additional outlay for the user since the first cover is automatically pushed back or pushed together when the catheter tube is pushed into the vein. By way of example, the first cover may be embodied in the form of a bag-like envelope or in the form of bellows.

A further peculiarity of the catheter according to the invention consists of the use of a small-lumen cannula being possible. This is advantageous in that the skin opening created by the puncture needle need not be substantially widened when pushing through the cannula. In particular, no dilatation within the conventional medical sense is required in the process. Therefore, the catheter according to the invention may also be realized without a dilatation cannula. Instead, the cannula has the function of securing the lumen created by the puncture needle. Therefore, it may also be referred to as lumen-securing cannula. According to an advantageous development of the invention, the outer diameter of the cannula is therefore at most twice as large as the outer diameter of the puncture needle. In an advantageous development, the outer diameter of the cannula is at most 1.5-times as large as the outer diameter of the puncture needle.

In contrast to other, known proposals, a puncture needle which has a smaller diameter than the catheter tube and consequently only leaves behind a small hole in the skin is therefore proposed.

Herein also lies a decisive advantage over known catheter solutions. In known systems, use is made of e.g. a cannula with a large diameter, through which the catheter tube is then inserted into the vein. The cannula may be left or optionally split and removed. In such systems, the puncture hole in the skin has a greater diameter than the catheter tube, as a result of which there is, as a rule, bleeding from the skin entry point of the catheter tube. Moreover, the diameter of the catheter tube to be inserted is restricted by the diameter of the cannula. Since the latter must already have a certain diameter, the diameter of the catheter tube is restricted, and so it is not possible to infuse particularly large quantities of liquid into the vein per unit time. A further disadvantage of known systems is that the puncture needle used for puncturing has an equally large diameter, and so the puncturing process is traumatizing. Puncture failures may have significant injuries as a consequence. Such disadvantages are overcome by the present invention.

Accordingly, only a small jump in diameter is present at the transition from the puncture needle to the cannula. In order to further simplify the introduction of the cannula, the latter may have a rounded embodiment at the patient-near end.

In respect to the catheter tube, a larger jump in diameter arises in comparison with the cannula; this is necessary in order also to realize a necessary inner diameter required for supplying large amounts of liquids. According to an advantageous development of the invention, the outer diameter of the catheter tube is therefore at least twice as large as the outer diameter of the cannula. As a result of this, large flow rates are ensured. According to an advantageous development of the invention, the outer diameter of the catheter tube is at least three times as large as the outer diameter of the cannula.

Accordingly, a dilatation step is only required when inserting the catheter tube into the vein.

According to an advantageous development of the invention, the catheter has at the patient-distant end an aspiration aid or an aspiration connector for connecting an aspiration aid. The aspiration aid which, for example, may be embodied as a conventional syringe may be connected to e.g. the puncture needle by way of the aspiration connector. In this case, it is advantageous to embody the puncture needle as a hollow needle such that liquids may be transported through the puncture needle. The aspiration aid or a further aspiration aid may also be connected to the cannula at the patient-distant end. In this way, the cannula may also be compatible at the patient-distant end with an aspiration aid or else other systems, e.g. tube systems; this is very helpful for differentiating between venous and arterial puncturing. A further essential advantage of the invention should be seen herein. By way of example, the user may connect an infusion tube and visually determine whether or not the blood rises in a pulsating manner in this infusion tube (arterial puncture). Moreover, it is easier to differentiate between venous and arterial puncturing, even in the case of patients with a non-pulsatile blood flow, e.g. in the case of implanted cardiac support systems.

According to an advantageous development of the invention, the catheter tube is arranged between the tip of the puncture needle and the aspiration connector or the aspiration aid.

According to an advantageous development of the invention, the catheter tube has a length of at least 12 cm; however, it may also have a longer embodiment for many applications.

According to an advantageous development of the invention, the catheter tube has a multi-lumen embodiment. This is advantageous in that, in addition to the work lumen, one or more lumens are still available, by means of which e.g. liquids can be transported separately or an ECG lead may be effectuated. Thus, for example, the catheter may be embodied with a work lumen and one or more auxiliary lumen(s), e.g. with lateral intravenous exits. According to an advantageous development of the invention, individual lumens are removable and/or complementable. As a result of this, a modular lumen system is created, said modular lumen system allowing lumen to be removed and/or complemented, either in advance or in the case of an already inserted catheter tube, for example for reducing the risk of infection if the catheter tube remains in the patient for a relatively long time.

According to an advantageous development of the invention, the cannula consists of a plastics material, in particular of a thermoplastic plastics material. As a result of this, the cannula may have a relatively flexible design but, nevertheless, is robust. Possible risks of injury are minimized thereby. The catheter tube may also consist of a plastics material. The puncture needle may advantageously be embodied as a metal needle.

According to an advantageous development of the invention, the cannula is longer than the catheter tube and/or the puncture needle is longer than the cannula. Accordingly, the cannula may protrude from the catheter tube at both sides and the puncture needle may protrude from the cannula at both sides. This simplifies the longitudinal displacement and removal of the puncture needle and the cannula, in each case from the patient-distant end of the catheter.

According to an advantageous development of the invention, the catheter has a second cover which is arranged at the patient-distant end of the catheter and which surrounds at least the region of the cannula that protrudes from the catheter tube at the patient-distant end of the catheter, and so the cannula is kept sterile in this region. The first cover and the second cover may be embodied as separate covers. Such a two-part protective sleeve is a further peculiarity of the catheter according to the invention. By way of example, the second cover may be embodied in the form of a bag-like envelope or in the form of bellows.

According to an advantageous development of the invention, the catheter has a hydrophobic surface, e.g. a surface in the style of a lotus effect, on its entire outer surface and/or inner surface or portions thereof. In this way, the catheter has blood-repellent properties in such regions at the same time. This is advantageous in that it is no longer possible for the lumen to be blocked by blood or clotted blood or secretion. Moreover, the catheter is improved from a hygienic and infectiological point of view. Moreover, the catheter is more comfortable and esthetic in use since collections of blood and contaminants no longer occur, even from the outside. Hence, the surface has a low wettability; liquids such as water and blood droplets drip off and, in the process, also carry along dirt particles on the surface.

In this way, a novel catheter is specified, said catheter having telescopic and lamellar-like properties. On account of its at least three-layer construction, the catheter stabilizes itself during the puncture process. On account of the increasing diameter of the layers from the inside to the outside, there is increasing expansion of the puncture channel without relatively large jumps in diameter. Here, the puncture needle may have a similarly thin embodiment to that in the Seldinger technique in order to traumatize tissue and vessels as little as possible in the case of a puncture failure. Behind the catheter tube at the patient-distant end of the catheter, it is possible to arrange a syringe for blood aspiration and for verifying the intravenous orientation. The cannula is introduced a defined length into the vein over the puncture needle immediately after blood aspiration. As a result, the risk of a dislocation of the puncture system from the vein is reduced. Thereupon, the catheter tube is advanced into the body over the cannula. A first cover that can be pushed back keeps the catheter tube sterile in the process. Said catheter tube has a dilatation body, for example made of a thermoplastic material, at the patient-near end. Consequently, it is possible to dispense with separate dilatation means. Therefore, significantly fewer work steps are required in contrast to the Seldinger technique. As a result of this, the risk of injury and infection is minimized for the patient and user. Complications caused by a Seldinger wire can no longer occur. The orientation of the catheter tube can be monitored continuously by means of an ECG lead. As a result of the simple handling with lower costs, new fields of application are opened up, such as e.g. preclinical emergency medicine.

Moreover, a type of "closed system" can be created using the first and/or second cover, said closed system being able to wholly meet the relevant hygiene aspects.

By way of example, the invention may be provided as a puncture set having the following components (length specifications are only exemplary and variable in practice):

1) 25 cm long puncture needle 20G, having a protective cap over the needle tip
2) 23.5 cm long cannula, e.g. in the form of a plastics cannula over the puncture needle with a patient-distant fixing flag (puncture needle and cannula are situated in the work lumen of the catheter tube)
3) 17 cm long catheter tube with dilatational properties (thermoplastic), three lumens, including one shorter work lumen 14-16G and two lumens with 12G each, with lateral intravenous exits, patient-distant extensions ("legs") and preassembled three-way valves, additionally clamps and wings for suturing,
4) Cap for closing the work lumen including the cannula; additional three-way valve for possible use of the work lumen as an additional infusion lumen after puncturing is complete
5) 10 ml syringe for blood aspiration (prefilled with 5 ml saline solution/distilled water)
6) Two syringes for flushing the legs after puncturing (each prefilled with 10 ml saline solution/distilled water)
7) Sterile envelope that can be pushed back for coating the catheter tube
8) Suturing set and scalpel In summary, the following further advantages emerge from the invention:

A cannula can be introduced into the vein immediately after blood aspiration. This reduces the risk of "slipping out" of the vessel again. The puncture needle may be removed immediately; no further movements are needed while the puncture needle lies in the body. This minimizes the risk of injury to the patient and the user. The introduction of the cannula causes comparatively little trauma, like the puncture itself; the risk of complications can be calculated in the case of an arterial puncture failure.

The cover that can be pushed back keeps the catheter tube sterile; sterile surroundings as described above are not required. The spatial requirements are minimal and emerge from the sum of the requirements of the person carrying out the puncturing and the set itself only.

The risk of accidental contacts between the sterile materials and the surroundings is minimized by virtue of the components being integrated into a puncture system, namely the catheter according to the invention. This reduces the risk of infection for the patient and user.

No Seldinger wire or other components, which could accidentally remain in the body or cause other complications, are required.

The orientation can be monitored continuously when advancing the catheter tube; if desired, the ECG signal can be led directly via the tip of the catheter tube. Moreover, the venous orientation of the catheter tube can be verified by blood aspiration via same at any time ("permanent lumen monitoring").

Many steps of the conventional Seldinger technique are no longer required (deconnections, threading, etc.); an assistant is not required.

The users are already well acquainted with the Braunüle®. This may help experienced users, in particular, to learn the novel puncture technique with the catheter according to the invention.

The system is sufficiently stable during puncturing despite the long puncture needle and it stabilizes itself on account of the lamella-like property.

The dilatation means are integrated into the catheter tube and have thermoplastic properties. The tip of the catheter tube may have a comparatively soft design since it only needs to use the already available puncture hole. The cannula is still situated in the puncture hole when the catheter tube is advanced. Only as a result of the dilatation bodies is a veritable "gentle dilatation" of the skin channel effectuated. Such a "gentle dilatation" may advantageously be promoted by a dilatation body that increases in a ramp-shaped manner, the diameter of which also increases only "gently", i.e. with a small gradient.

The tip of the catheter tube may consist of a soft and hence tissue-sparing material since the dilatation of the skin channel and of the vein wall is only effectuated by the subsequent dilatation body. Since this dilatation body only follows the soft tip, only a very small risk of injury emanates from the dilatation body when the latter is oriented in the tissue or in the vein. The risk of injury is further reduced by the just described thermoplastic properties of the dilatation body. The dilatation body may have a small "gradient of increase" and consequently facilitate a very "gentle" dilatation.

The technique may be used in the preclinical field.

Increased costs at the beginning of the development can be compensated by savings at a different point (little time outlay, minimization of the risk of sterile material falling down, with necessary replacements during the procedure, etc.).

Puncturing any relatively large vein is possible using the novel puncture system, even if, primarily, a central venous orientation of the tip of the catheter tube is not mandatory. However, the latter can be obtained without problems. On account of the option of applying a multi-lumen system with high flow rates without the necessity of applying sterile surroundings, the following application options, for example, emerge:

preclinical emergency medicine with a focus on trauma care
in-hospital emergency medicine
intensive care medicine
dialysis, e.g. in intensive care units
anesthesiology with a focus on large surgical interventions with significant volume losses
medicine in war zones, crisis areas and disaster zones
medicine in spatially restricted conditions (airplanes, ground-based protection and emergency vehicles, ships, etc.).

The novel puncture system has telescopic and lamella-like properties. A type of catheter-over-needle technique is effectuated twice, directly in succession, on a puncture system. This results in a completely novel puncture technique. The puncture channel is initially small, as a result of which the risk of complications on account of puncture failure is manageable. Until now, this advantage was reserved for the Seldinger technique since it was only the latter that allowed the introduction of a large catheter tube through a small puncture channel by way of dilatation of the latter via various intermediate steps.

In the novel puncture system, the catheter tube is situated, for example, between the tip of the puncture needle and the syringe for blood aspiration. A few millimeters proximal of the tip of the catheter tube, a more solid component may be embedded in the latter, the length of which likewise only is a few millimeters. It has dilatational properties and consequently replaces the dilatation means used in the Seldinger technique. An injury to the vein wall is very unlikely since the more solid component itself does not have sharp properties and only follows the softer tip of the catheter tube. Moreover, the dilatational component may also have thermoplastic properties such that it becomes softer in the body and is no longer able to irritate the surrounding structures in a relevant manner.

Since, after a vein has been punctured, a cannula may initially be introduced a few centimeters into the vein and the puncture needle may be immediately withdrawn or removed, the intravenous orientation prior to introduction of the catheter tube may be effectively secured. There no longer is a risk of injury as a result of an inserted sharp puncture needle when introducing the catheter tube. As a result, patient safety is improved. The risk of injury to the user is likewise minimized since all components are integrated into a puncture system and fewer work steps are required. This also reduces the risk of infection for the patient and user. The cover that can be pushed back keeps the catheter tube sterile; sterile surroundings like in the conventional Seldinger technique are not required. This promotes all types of application, for example in the preclinical field.

Likewise, there no longer is the risk of injuring e.g. the heart by way of a Seldinger wire that is introduced very far; moreover, the probability of arrhythmia is very low since the cannula is only situated far enough in the vein to secure the intravenous orientation and make the way into the vein for the following catheter tube. In comparison with the Seldinger technique, the catheter tube is no longer guided directly in front of the heart by way of a wire. This also does not appear necessary if the catheter tube, guided by the cannula, securely lies intravenously and has taken up the "correct direction" (toward the heart). Then, it can be advanced safely in the direction of the heart. It must be noted that incorrect orientations frequently occur within the scope of the Seldinger technique and wrong ways are then also followed very consequently with the aid of the wire. In the case of the invention, there can now be a continuous ECG lead for already monitoring the orientation during the advance of the catheter tube. Consequently, the uncertainty in the orientation of the Seldinger wire existing when the latter is introduced in the case of the Seldinger technique no longer applies.

The invention allows renewed monitoring of the venous orientation after the introduction of the cannula and before the introduction of the catheter tube, including the dilatational component. As a result, it is possible, once again, to identify an arterial puncture failure/extravascular orientation of the system before dilatation takes place. The risk of complications is further reduced as a result thereof. Should the initially introduced cannula have an incorrect orientation, the risk is manageable as it does not yet have a large lumen. An arterial puncture failure may be noticed even without aspiration under certain circumstances since, as a rule, bright blood will pulsate out of the cannula after removal of the puncture needle or said blood will flow out quickly despite the long catheter. The cannula cannot remain in the body by accident since, for structural reasons, said cannula is prevented from entering the body by a proximal flag.

Many steps of the conventional Seldinger technique are no longer required. It is possible to dispense with deconnection and reconnection/threading steps. This reduces the complexity of the method; moreover, it is possible to save staff and material costs.

In summary, the novel puncture system allows a large catheter tube to be introduced directly and securely into a vein close to the heart by way of an initially small puncture channel. The risk of injury and infection for the patient and user are minimized; there no longer are risks from an inserted Seldinger wire. The orientation of the catheter tube can be monitored continuously. The novel puncture system allows simple handling; costs may be saved.

The invention may advantageously be developed by the following features:

- An ECG lead for monitoring the orientation of the patient-near end of the catheter tube in a simplified form by way of a monitor on the chest which only captures simple ECG signals; this method is applicable everywhere, even in preclinical and in-hospital emergency medicine settings.
- A removable lumen/modular/complementable system in order to reduce the risk of infection if the central venous catheter remains for a relatively long time duration.
- A semiautomatic system which independently indicates the position of the patient-near end of the catheter tube.
- An electrically conductive, metallized syringe and/or catheter tube with electrically conductive properties for the ECG lead.
- A traffic light system on the central venous catheter (multicolored central venous catheter) and on the set packaging (1-2-3, red-amber-green) for simplified operability, even for beginners/inexperienced people.
- A system for automatically evaluating the blood flows from the patient-near end of the catheter tube ("fully automatic machine").
- A system for determining the position of the patient-near end of the catheter tube by measuring a current; the central venous catheter no longer needs to be introduced "too deep" at the outset.
- A system for continuously or intermittently monitoring the orientation of the patient-near end of the catheter tube, even for a general ward.
- An integrated Doppler system for detecting an arterial and venous orientation and venous air embolisms within the scope of neurosurgical interventions in a seated position, with automatic aspiration of the air via a further distal hole or via further additional holes.
- A self-closing lumen after an interior cannula was removed; this facilitates higher flow rates through the other lumens.
- A puncture needle which is not hard at the patient-distant component. As a result, the puncture needle cannot be introduced too far into the vein.
- A puncture needle consisting of a hard plastic which becomes soft when the puncture needle is advanced (or else when the fixing flag is withdrawn, a connection between the puncture needle and the cannula existing in this case).
- A puncture needle connected with the tip by way of a connector; the catheter tube is wound in a loop-like manner.
- The fixation of the central venous catheter is effectuated by way of a special "click mechanism" with clamps on the skin; suturing is no longer necessary.

A lubricant in the patient-near (first) cover. As a result of this, the catheter tube can be guided more easily through the skin and into the vein.

BRIEF DESCRIPTION OF THE DRAWINGS

The invention will be explained in more detail below on the basis of exemplary embodiments, with use being made of drawings.

In the figures.

DETAILED DESCRIPTION

In the figures, the same reference signs are used for elements that correspond to one another.

Figure 1:
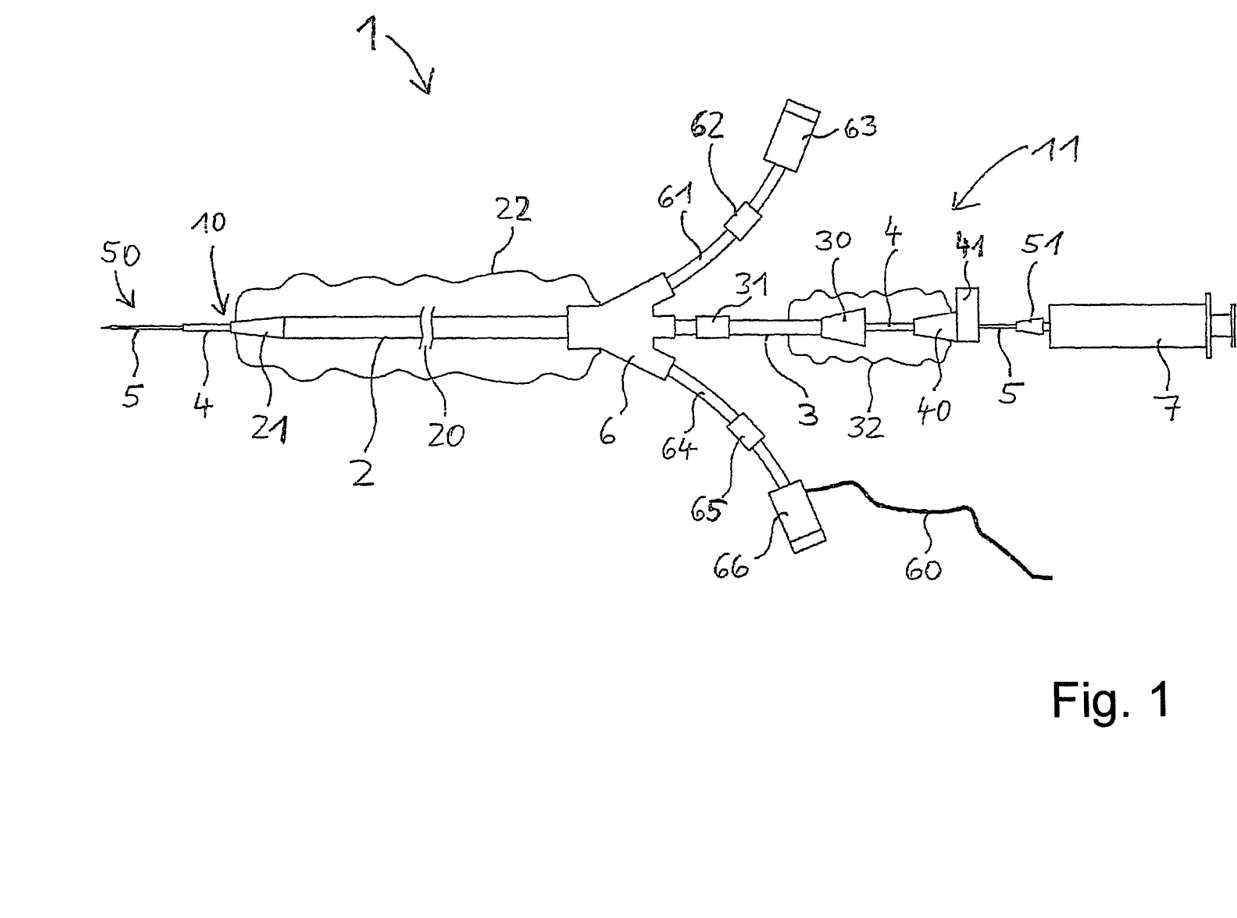
FIG. 1 shows a central venous catheter in a first embodiment.

FIG. 1 shows the basic structure of the catheter 1 according to the invention. The assumption is made that, in the supplied state, all lumens are already prefilled with sterile saline and/or distilled water so that the catheter 1 can be used directly without venting. The catheter 1 and also further components forming the puncture system should be supplied in sterile packaging in the illustrated form and can be used immediately without further preparation after the packaging is opened. Opening under sterile conditions is not required.

The catheter 1 has a patient-near end 10, at which parts of the catheter 1 should be introduced into a vein of a patient. Further, the catheter 1 has a patient-distant end 11 which, as may be identified, is arranged at the end region of the catheter 1 distant from the patient-near end 10. The catheter 1 is operated by a user at the patient-distant end 11.

The catheter 1 has a catheter tube 2, a work lumen 3, a cannula 4 and a puncture needle 5. The cannula 4 is guided longitudinally through the catheter tube 2 or the work lumen 3 within the work lumen 3 of the catheter tube 2. The puncture needle 5 is guided longitudinally through the cannula 4 within the cannula 4. At the patient-near end 10, the puncture needle 5 protrudes from the catheter 1 with a puncturing portion 50. Here, FIG. 1 shows that the cannula 4 is already pushed out of the catheter tube 2; initially, i.e. in the supplied state of the catheter 1, this is not the case. This case only occurs within the scope of applying the catheter 1 to a patient, as will still be explained below. Initially, only the puncturing portion 50 of the puncture needle 5 protrudes from the catheter 1 at the patient-near end 10. Initially, i.e. in the supplied state, the puncturing portion 50 is protected from non-sterile influences by means of, for example, a protective cap, as is used in syringe cannulas.

The catheter 1 has a relatively long embodiment, with the catheter 1 being reproduced in a shortened manner in the central region in FIG. 1; this is intended to be symbolized by the marking 20. In fact, the catheter 1 may have significantly longer proportions.

The catheter 1 has a multi-lumen embodiment. In addition to the work lumen 3, it still has a first auxiliary lumen 61 with a first catheter attachment 63 and a second auxiliary lumen 64 with a second catheter attachment 66. The work lumen 3 and the auxiliary lumens 61, 64 are merged by way of a connection portion 6, which may also be used as a fixing wing of the catheter for attachment to a patient, and coupled to the catheter tube 2. The auxiliary lumens 61, 64 have a conventional embodiment as in the case of known central venous catheters, for example in the form of a respective tube 61, 64, a tube clamp 62, 65 for clamping the tube 61, 64 and a connection body, also referred to as catheter attachment, by means of which a syringe or a tube can be connected to one of the auxiliary lumens 61, 64 in each case. By way of example, an electrical connection line 60 for a discrete continuous ECG lead via the catheter tube may be present at the second auxiliary lumen 64.

As may also be identified from FIG. 1, the catheter tube 2 has a relatively large jump in diameter in comparison with the cannula 4. Therefore, a dilatational step is required for inserting the catheter tube 2 into the vein. To this end, a dilatation body 21, which may be embodied in the form of a beveled end of the catheter tube 2, is situated at the patient-near end 10 at the end of the catheter tube 2.

In order to keep the catheter tube 2 sterile prior to the introduction into the vein, said catheter tube is surrounded by a first cover 22 in the form of a bag-like envelope. The latter extends from the patient-near end 10 to the connection portion 6. At the patient-near end 10, the first cover 22 is arranged in a displaceable manner on the catheter tube 2 and automatically pushed back by the skin contact when the catheter tube 2 is advanced into the vein of a patient.

At the patient-distant end 11, a tube clamp 31 is arranged on the work lumen 3, said tube clamp serving to clamp the work lumen 3, at least after the cannula 4 and the puncture needle 5 were removed therefrom.

At the patient-distant end 11, the work lumen 3 ends with a termination piece 30. The latter serves as a stop for the advance of the cannula 4 in order to ensure that the cannula 4 cannot be advanced to an unwanted far extent. At the patient-distant end 11, the cannula 4 ends with a termination piece 40, on which a fixing flag 41 is arranged. The fixing flag 41 serves to prevent the middle layer, i.e. the cannula 4, from being able to be advanced excessively far into the vein. This should avoid the cannula 4 inadvertently remaining in the body or irritating the heart when it protrudes too far out of the catheter tube 2 and the catheter tube 2 is advanced in the direction of the heart. Additionally, the fixing flag 41 can be used for a manual grip when advancing or withdrawing the cannula 4; therefore, it also acts as an actuation means of the cannula 4 at the same time. Toward the front, the cannula 4 can be advanced in the direction of the patient-near end 10 until the termination piece 40 comes to rest at the termination piece 30.

The catheter 1 has a second cover 32 in the form of a bag-like envelope which surrounds the open region of the cannula 4 at the patient-distant end 11 in order to keep said region sterile. Consequently, the puncture system according to the invention may be embodied with a sterile cover that is split in two, namely the first cover 22 which is situated distally toward the patient at the puncture system and, additionally, the second cover 32, which is situated proximally, further away from the patient, where the inner tubular body 4 protrudes from the outer tubular body 2 before puncturing. Here, the patient-near part of the cover, i.e. the first cover 22, in particular, may have a sterile lubricating gel, by means of which the friction when advancing the outer tubular body into the body part of the living being and, in particular, through the skin is minimized.

At the patient-distant end 11, the puncture needle 5 protrudes from the cannula 4. By way of example, it has a connection body 51 for connecting a syringe 7. The syringe 7 or connection body 51 may be used simultaneously as an actuation means for withdrawing the puncture needle 5 after the cannula 4 has been inserted into the vein. A blood aspiration may be performed by means of the syringe 7.

When applying the catheter 1 according to FIG. 1 to a patient, the following procedure may advantageously be carried out:

1) puncturing the vein with the puncture needle
2) advancing the cannula into the vein if venous blood is aspirated; here, the advance is effectuated at the fixing flag until the latter cannot be advanced any further, i.e. it has reached the work lumen (it deliberately does not fit into the latter)
3) removing the puncture needle
4) immediately closing the cannula or checking the correct intravenous orientation again using a syringe
5) advancing the catheter tube over the cannula into the vein
6) removing the cannula
7) fixing the catheter tube to the skin when necessary.

Figure 2:
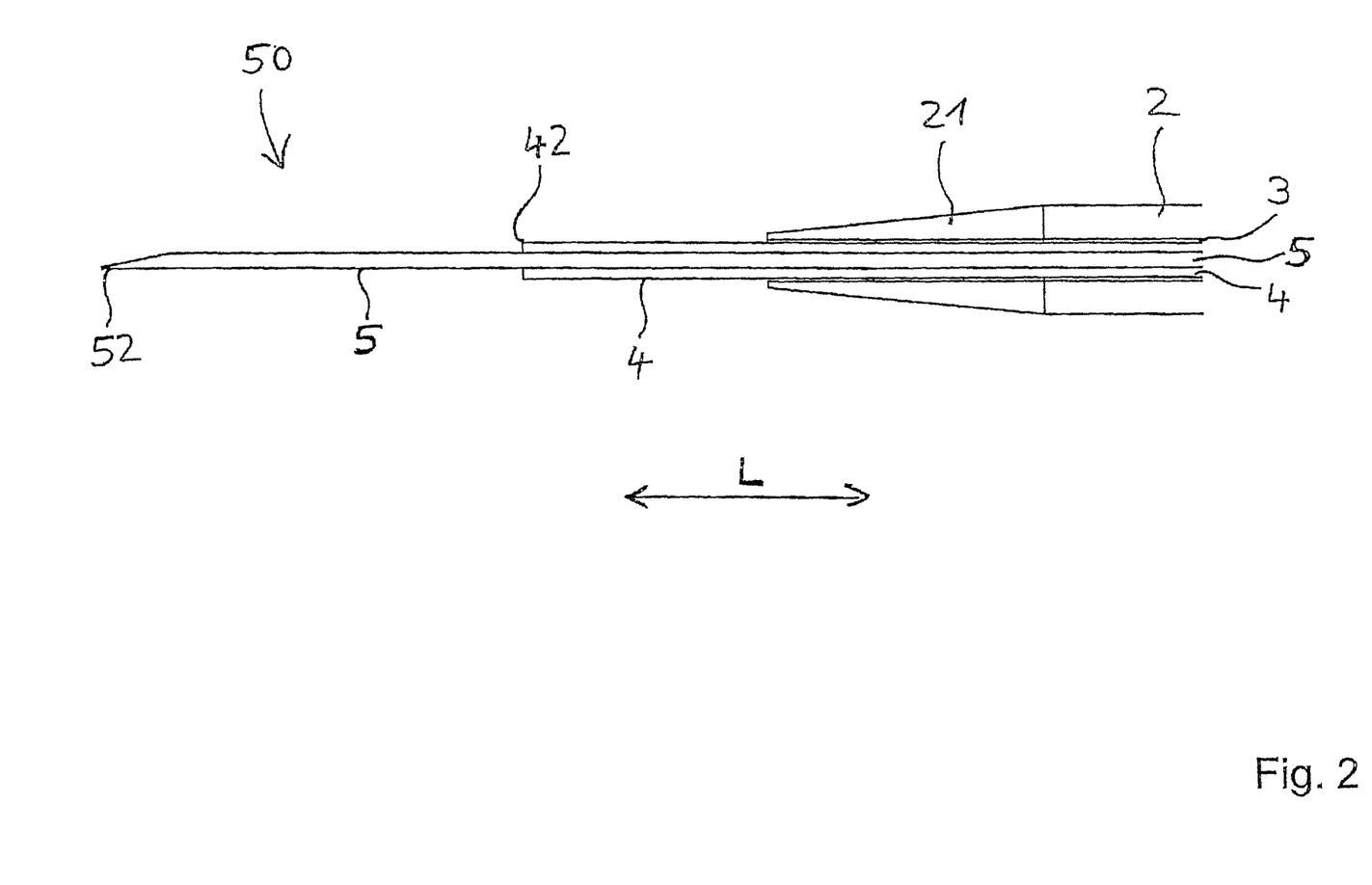
FIG. 2 shows a magnified detailed illustration of the patient-near end of the catheter according to FIG. 1.

FIG. 2 shows the details of the patient-near end 10 of the catheter 1 in a magnified sectional illustration. It is possible to identify the at least three-layer construction, in which the cannula 4 is arranged within the catheter tube 2 or within the work lumen 3 thereof, and in which the puncture needle 5 is arranged within the cannula 4. The puncture needle 5 is displaceable in the direction of the longitudinal axis L, i.e. longitudinally displaceable. The cannula 4 is likewise displaceable in the direction of the longitudinal axis L, i.e. longitudinally displaceable. The work lumen 3 may be securely connected to the catheter tube 2 in this case. By way of example, the cannula 4 may have a rounded embodiment at its patient-near end 42 in order to ease the introduction into the vein. The puncture needle 5 has a tip 52 at the end, like in the case of injection cannulas.

Figure 3:
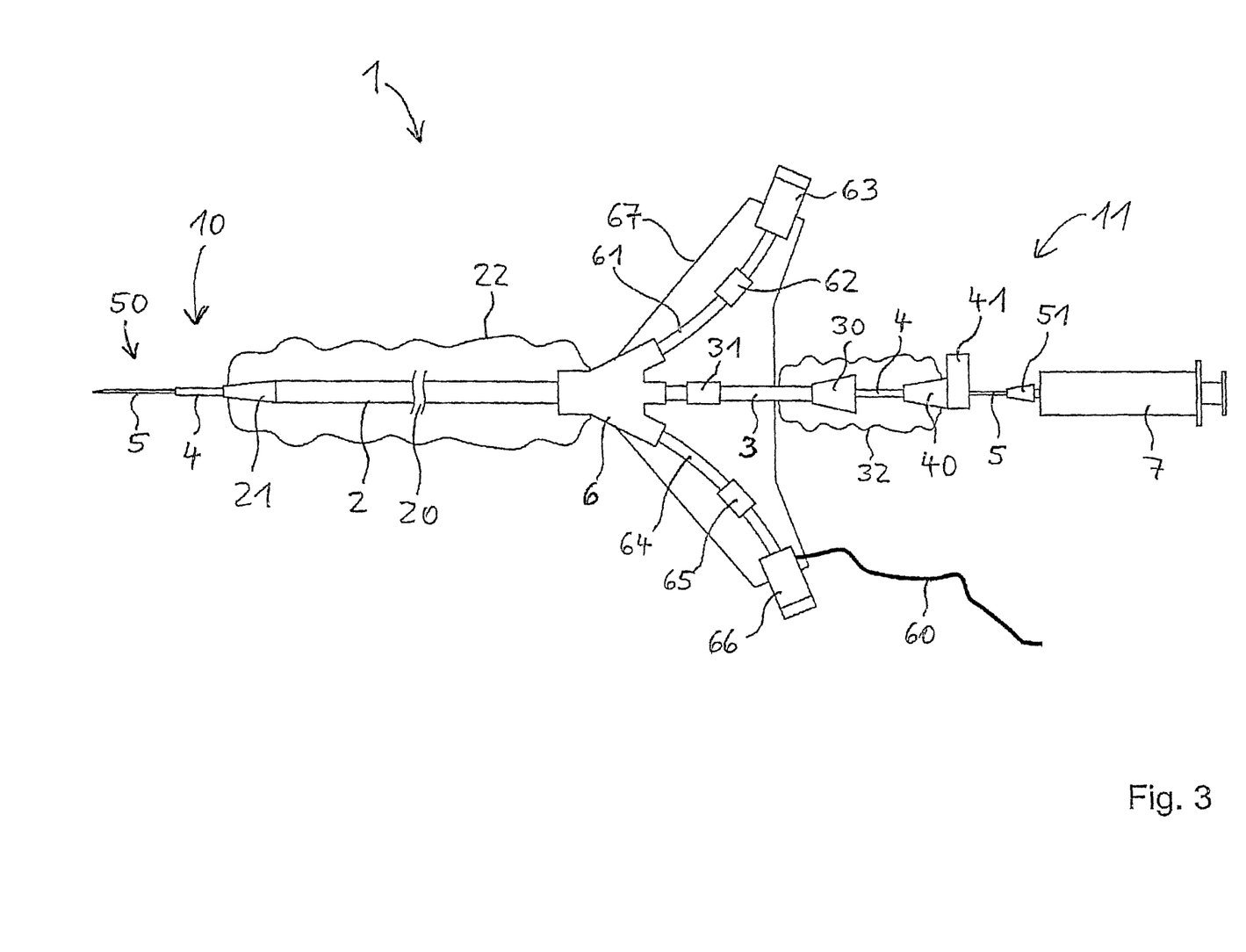
FIG. 3 shows a second embodiment of a central venous catheter.

FIG. 3 shows an embodiment of the catheter 1, which, in comparison with the embodiment in FIG. 1, has been complemented by a holding means 67, on which the three legs emerging from the connection portion 6, i.e. the work lumen 3 and the auxiliary lumens 61, 64 and the parts connected therewith, may be fully or partly fixed. This simplifies the handling since these legs are no longer able to move loosely but remain in predefined positions. By way of example, the holding means 67 can be embodied in the form of a holding plate, for example in a triangular form or a similar form.

In a complementary manner, a holding body may be arranged at the patient-near end 10 of the catheter 1, said holding body allowing the user to hold and control or further stabilize the patient-near end 10 of the catheter 1 with the second hand during puncturing. This holding body may be applied to the catheter 1 in a displaceable manner in relation to the catheter tube 2 and may thus be kept at a fixed position when the catheter tube 2 is inserted into the body. Additionally, the holding body may contain wings, in a manner similar to a commercially available cannula that remains in peripheral veins, the catheter 1 being able to be fixed additionally thereon, for example by way of suturing. However, the holding body may also be removed at the end of the introduction process, i.e. it may be detachably fastened to the catheter 1.

The invention claimed is:

1. A puncture system, comprising:
   an outer tubular body configured to remain in a body part of a living being;
   an inner tubular body;
   a puncture needle; and
   a dilatation body at a patient-near end that increases in a ramp-shaped manner, wherein the inner tubular body is configured to be guided through the dilatation body,
   wherein the inner tubular body is configured to be guided through a work lumen of the outer tubular body and to be longitudinally displaceable in relation to the outer tubular body,
   wherein the puncture needle is configured to be guided through a puncture lumen of the inner tubular body,
   wherein the inner tubular body is configured to be longitudinally displaceable in relation to the puncture needle,
   wherein the puncture system is configured such that, after puncturing the body part by a puncturing portion of the puncture needle protruding from the patient-near end of the puncture system, the inner tubular body is able to be pushed, at least in part, out of the outer tubular body from the patient-near end of the puncture system, and, wherein the inner tubular body is configured to receive the puncturing portion of the puncture needle protruding from the patient-near end of the puncture system, at least in part, in the puncture lumen of the inner tubular body,
   wherein an outer diameter of the inner tubular body is no more than twice as large as an outer diameter of the puncture needle and wherein the inner tubular body is flexible, wherein size and flexibility of the inner tubular body permit the inner tubular body to advance forward intravenously along a lumen of a vein,
   wherein an outer diameter of the outer tubular body is at least twice as large as an outer diameter of the inner tubular body such that the outer tubular body accommodates an inner diameter for supplying liquids, and
   wherein the inner tubular body is configured to be pulled out of the outer tubular body at a patient-distant end to remove the inner tubular body from the body part of the living being.

2. The puncture system as claimed in claim 1 wherein the puncture system is configured such that a longitudinal displacement of the outer tubular body in relation to the inner tubular body and a longitudinal displacement of the inner tubular body in relation to the puncture needle is controllable independently of one another in each case by an actuator at a patient-distant end of the puncture system.

3. The puncture system as claimed in claim 1 wherein the puncture system does not have a dilatation cannula.

4. The puncture system as claimed in claim 1, wherein the dilatation body is configured to be longitudinally displaceable in relation to the inner tubular body.

5. The puncture system as claimed in claim 1, wherein the dilatation body is fastened to at least one of the outer tubular body or part of the outer tubular body.

6. The puncture system as claimed in claim 1 wherein the outer tubular body is surrounded by a first cover which keeps the outer tubular body sterile outside of the body part.

7. The puncture system as claimed in claim 1 wherein at least one of the puncture needle and the inner tubular body has at a patient-distant end an aspiration aid or an aspiration connector for connecting the aspiration aid.

8. The puncture system as claimed in claim 1 wherein the inner tubular body consists of a plastics material.

9. The puncture system as claimed in claim 1 wherein the inner tubular body is longer than the outer tubular body and/or the puncture needle is longer than the inner tubular body.

10. A puncture system, comprising:
    an outer tubular body configured to remain in a body part of a living being;
    an inner tubular body; and
    a puncture needle, wherein the inner tubular body is configured to be guided through a work lumen of the outer tubular body and to be longitudinally displaceable in relation to the outer tubular body, wherein the puncture needle is configured to be guided through a puncture lumen of the inner tubular body, wherein the inner tubular body is configured to be longitudinally displaceable in relation to the puncture needle, wherein the puncture system is configured such that, after puncturing the body part by a puncturing portion of the puncture needle protruding from a patient-near end of the puncture system, the inner tubular body is able to be pushed, at least in part, out of the outer tubular body from the patient-near end of the puncture system, and, wherein the inner tubular body is configured to receive the puncturing portion of the puncture needle protruding from the patient-near end of the puncture system, at least in part, in the puncture lumen of the inner tubular body, wherein an outer diameter of the inner tubular body is no more than twice as large as an outer diameter of the puncture needle and wherein the inner tubular body is flexible, wherein size and flexibility of the inner tubular body permit the inner tubular body to advance forward intravenously along a lumen of a vein, wherein an outer diameter of the outer tubular body is at least twice as large as an outer diameter of the inner tubular body such that the outer tubular body accommodates an inner diameter for supplying liquids, wherein the inner tubular body is configured to be pulled out of the outer tubular body at a patient-distant end to remove the inner tubular body from the body part of the living being, and wherein the outer tubular body has a multi-lumen configuration wherein individual lumens are removable and/or complementable.

11. A puncture system, comprising:

an outer tubular body configured to remain in a body part of a living being;

an inner tubular body; and a puncture needle, wherein the inner tubular body is configured to be guided through a work lumen of the outer tubular body and to be longitudinally displaceable in relation to the outer tubular body, wherein the puncture needle is configured to be guided through a puncture lumen of the inner tubular body, wherein the inner tubular body is configured to be longitudinally displaceable in relation to the puncture needle, wherein the puncture system is configured such that, after puncturing the body part by a puncturing portion of the puncture needle protruding from a patient-near end of the puncture system, the inner tubular body is able to be pushed, at least in part, out of the outer tubular body from the patient-near end of the puncture system, and, wherein the inner tubular body is configured to receive the puncturing portion of the puncture needle protruding from the patient-near end of the puncture system, at least in part, in the puncture lumen of the inner tubular body, wherein an outer diameter of the inner tubular body is no more than twice as large as an outer diameter of the puncture needle and wherein the inner tubular body is flexible, wherein size and flexibility of the inner tubular body permit the inner tubular body to advance forward intravenously along a lumen of a vein, wherein an outer diameter of the outer tubular body is at least twice as large as an outer diameter of the inner tubular body such that the outer tubular body accommodates an inner diameter for supplying liquids, wherein the inner tubular body is configured to be pulled out of the outer tubular body at a patient-distant end to remove the inner tubular body from the body part of the living being, and wherein the outer tubular body is rigid.

* * * * *